(12) United States Patent
Li et al.

(10) Patent No.: US 11,534,272 B2
(45) Date of Patent: Dec. 27, 2022

(54) MACHINE LEARNING SCORING SYSTEM AND METHODS FOR TOOTH POSITION ASSESSMENT

(71) Applicant: Align Technology, Inc., San Jose, CA (US)

(72) Inventors: Guotu Li, Durham, NC (US); Christopher E. Cramer, Durham, NC (US); Chad Clayton Brown, Cary, NC (US); Anton Spiridonov, Cary, NC (US)

(73) Assignee: Align Technology, Inc., San Jose, CA (US)

( * ) Notice: Subject to any disclaimer, the term of this patent is extended or adjusted under 35 U.S.C. 154(b) by 509 days.

(21) Appl. No.: 16/569,345

(22) Filed: Sep. 12, 2019

(65) Prior Publication Data

US 2020/0085546 A1 Mar. 19, 2020

Related U.S. Application Data

(60) Provisional application No. 62/731,741, filed on Sep. 14, 2018.

(51) Int. Cl.
*A61C 9/00* (2006.01)
*A61C 13/34* (2006.01)
*A61B 5/00* (2006.01)
*A61C 13/20* (2006.01)
*A61C 7/00* (2006.01)

(52) U.S. Cl.
CPC .......... *A61C 9/0053* (2013.01); *A61B 5/0088* (2013.01); *A61B 5/7264* (2013.01); *A61C 7/002* (2013.01); *A61C 13/20* (2013.01); *A61C 13/34* (2013.01)

(58) Field of Classification Search
CPC ....... A61C 9/0053; A61C 7/002; A61C 13/20; A61C 13/34; A61B 5/0088; A61B 5/7264
USPC ......................................................... 382/128
See application file for complete search history.

(56) References Cited

U.S. PATENT DOCUMENTS

| | | |
|---|---|---|
| 5,975,893 A | 11/1999 | Chishti et al. |
| 6,227,850 B1 | 5/2001 | Chishti et al. |
| 6,227,851 B1 | 5/2001 | Chishti et al. |
| 6,299,440 B1 | 10/2001 | Phan et al. |
| 6,318,994 B1 | 11/2001 | Chishti et al. |
| 6,371,761 B1 | 4/2002 | Cheang et al. |
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,554,611 B2 | 4/2003 | Chishti et al. |
| 6,582,229 B1 | 6/2003 | Miller et al. |
| 6,602,070 B2 | 8/2003 | Miller et al. |

(Continued)

*Primary Examiner* — Michael R Neff
(74) *Attorney, Agent, or Firm* — Shay Glenn LLP

(57) ABSTRACT

Provided herein are systems and methods for scoring a post-treatment tooth position of a patient's teeth. A patient's dentition may be scanned and/or segmented. Raw dental features, principal component analysis (PCA) features, and/or or other features may be extracted and compared to those of other teeth, such as those obtained through automated machine learning systems. A classifier can identify and/or output the post-treatment tooth position of the patient's teeth.

24 Claims, 11 Drawing Sheets

(56) References Cited

U.S. PATENT DOCUMENTS

| | | |
|---|---|---|
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 9,814,549 B2 * | 11/2017 | Lee .................. A61C 13/0004 |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,096,763 B2 | 8/2021 | Akopov et al. |
| 11,116,605 B2 | 9/2021 | Nyukhtikov et al. |
| 11,147,652 B2 | 10/2021 | Mason et al. |
| 11,151,753 B2 | 10/2021 | Gao et al. |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2003/0219692 A1 * | 11/2003 | Kopelman .............. A61C 7/00 433/24 |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0306724 A1 | 12/2008 | Kitching et al. |
| 2010/0009308 A1 | 1/2010 | Wen et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2011/0191075 A1 * | 8/2011 | Hultgren ................ G06G 7/60 703/2 |
| 2013/0204599 A1 | 8/2013 | Matov et al. |
| 2016/0242870 A1 | 8/2016 | Matov et al. |
| 2016/0310235 A1 | 10/2016 | Derakhshan et al. |
| 2017/0103569 A1 * | 4/2017 | Wu ....................... G06T 15/04 |
| 2017/0273760 A1 | 9/2017 | Morton et al. |
| 2018/0280118 A1 | 10/2018 | Cramer |
| 2019/0029784 A1 | 1/2019 | Moalem et al. |
| 2019/0053876 A1 | 2/2019 | Sterental et al. |
| 2019/0192259 A1 | 6/2019 | Kopelman et al. |
| 2019/0328487 A1 | 10/2019 | Levin et al. |
| 2019/0328488 A1 | 10/2019 | Levin et al. |
| 2019/0333622 A1 | 10/2019 | Levin et al. |
| 2019/0343601 A1 | 11/2019 | Roschin et al. |
| 2020/0000552 A1 | 1/2020 | Mednikov et al. |
| 2020/0000554 A1 | 1/2020 | Makarenkova et al. |
| 2020/0000555 A1 | 1/2020 | Yuryev et al. |
| 2020/0107915 A1 | 4/2020 | Roschin et al. |
| 2020/0155274 A1 | 5/2020 | Pimenov et al. |
| 2020/0214800 A1 | 7/2020 | Matov et al. |
| 2020/0297458 A1 | 9/2020 | Roschin et al. |
| 2020/0306011 A1 | 10/2020 | Chekhonin et al. |
| 2020/0306012 A1 | 10/2020 | Roschin et al. |
| 2020/0315744 A1 | 10/2020 | Cramer |
| 2020/0360109 A1 | 11/2020 | Gao et al. |
| 2021/0073998 A1 | 3/2021 | Brown et al. |
| 2021/0134436 A1 | 5/2021 | Meyer et al. |
| 2021/0174477 A1 | 6/2021 | Shi et al. |

* cited by examiner

MACHINE LEARNING SCORING SYSTEM AND METHODS FOR TOOTH POSITION ASSESSMENT

CROSS REFERENCE TO RELATED APPLICATIONS

This patent application claims priority to U.S. Provisional Patent Application No. 62/731,741, filed on Sep. 14, 2018, titled "MACHINE LEARNING SCORING SYSTEM AND METHODS FOR TOOTH POSITION ASSESSMENT", and is herein incorporated by reference in its entirety.

INCORPORATION BY REFERENCE

All publications and patent applications mentioned in this specification are incorporated herein by reference in their entirety to the same extent as if each individual publication or patent application was specifically and individually indicated to be incorporated by reference.

BACKGROUND

Orthodontic procedures typically involve repositioning a patient's teeth to a desired arrangement in order to correct malocclusions and/or improve aesthetics. To achieve these objectives, orthodontic appliances such as braces, shell aligners, and the like can be applied to the patient's teeth by an orthodontic practitioner and/or by the patients themselves. The appliance can be configured to exert force on one or more teeth in order to effect desired tooth movements according to a treatment plan.

Orthodontic aligners may include devices that are removable and/or replaceable over the teeth. Orthodontic aligners may be provided as part of an orthodontic treatment plan. In some orthodontic treatment plans involving removable and/or replaceable aligners, a patient may be provided plurality of orthodontic aligners over the course of treatment to make incremental position adjustments to the patient's teeth. An orthodontic aligner may have a polymeric trough with an inner cavity shaped to receive and resiliently reposition teeth from one tooth arrangement to a successive tooth arrangement. Orthodontic aligners may include "active" regions that impose repositioning forces on teeth and "passive" regions that retain teeth in their current state.

Many orthodontic treatment plans, including at least some of those that involve removable and/or replaceable appliances that provide incremental forces on teeth over time, include a determination of post-treatment tooth position. The post-treatment tooth position can be used by a practitioner during treatment to guide the treatment plan. Existing systems tried to provide post-treatment tooth positions based on the raw vector of tooth point measurements, which turned out to be difficult due to multiple reasons: e.g., the rigid body constraints for each tooth, tooth collision, missing tooth/teeth handling etc. There is therefore a need for more accurately assessing and determining post-treatment tooth positions and generating recommendations for patients' post-treatment tooth positions.

SUMMARY OF THE DISCLOSURE

Implementations address the need to provide an automated tooth position scoring system to automatically, effectively, and accurately assess post-treatment tooth position, with a high degree of accuracy and a focus on post-treatment tooth positions that will be doctor-accepted. The present application addresses these and other technical problems by providing technical solutions and/or automated agents that automatically scoring post-treatment tooth positions in dental patients. Automatic tooth position scoring may provide the basis for implementation of automated orthodontic treatment plans, design and/or manufacture of orthodontic aligners (including series of polymeric orthodontic aligners that provide forces to correct malocclusions in patients' teeth). These apparatuses and/or methods may provide or modify a treatment plan, including an orthodontic treatment plan. The apparatuses and/or methods described herein may provide instructions to generate and/or may generate a set or series of aligners, and/or orthodontic treatment plans using orthodontic aligners that incorporate post-treatment tooth position scoring. The apparatuses and/or methods described herein may provide a visual representation of the patient's teeth including the post-treatment tooth position scoring.

In general, example apparatuses (e.g., devices, systems, etc.) and/or methods described herein may acquire a representation of a patient's teeth including tooth characteristics for use as the raw features in the scoring model. The raw features may be extracted from a 3D model of the patient's teeth (e.g., a 3D tooth point cloud). In some implementations, a subset of the 3D tooth point cloud (e.g., a specific number of points representing each tooth) can be used as the raw features.

Furthermore, example apparatuses (e.g., devices, systems, etc.) and/or methods described herein may further apply pre-processing to the raw features for the scoring model. For example, automated agents may identify, from the raw features, missing teeth, teeth that need to be extracted, teeth flagged as "DO NOT MOVE" a treatment, and other requirements in treatment prescriptions. The preprocessing can provide a modified set of raw features to the scoring model for post-treatment tooth position scoring.

In general, example apparatuses (e.g., devices, systems, etc.) and/or methods described herein may implement feature engineering with the raw features to build the scoring model that provides a score for post-treatment tooth positioning. There are many approaches to do feature engineering for building a scoring model, including hand designed features with a Principle Component Analysis (PCA) (e.g., PCA of tooth shapes, PCA of arch shapes, and smoothness measures of arches etc.), automated feature exploration (e.g., using deep neural networks or other feature selection methods), and a hybrid feature engineering approach, namely combining hand designed features and automated feature exploration model architecture.

In one example, a two-part feature engineering process is implemented by automated agents. This two-part process can first include formatting the raw feature data into a data structure that can allow a machine learning algorithm to account for neighboring teeth dependency and regional arch properties. In this example, the raw feature data can be formatted into a RGB image-like data structure. The second step of the two-part process can include machine learning operation on the RGB image-like data structure, which allows automated feature exploration of neighboring teeth dependency and local/regional arch shape.

In general, example apparatuses (e.g., devices, systems, etc.) and/or methods described herein may use machine learning classification models with the engineered feature data to return a score on the post-treatment tooth position of the patient. Examples of machine learning systems that may be used include, but are not limited to, Convolutional Neural Networks (CNN), Decision Tree, Random Forest, Logistic Regression, Support Vector Machine, AdaBoosT, K-Nearest Neighbor (KNN), Quadratic Discriminant Analysis, Neural Network, etc. The machine learning classification models can be configured to apply ground truth labeling when generating an output data set or post-treatment tooth positioning score. In some examples, the machine learning classification model can output a binary scoring label (e.g., output of 1 for a final tooth position likely to be accepted by a doctor and output of 0 for a final tooth position likely to be rejected by a doctor). In another example, the machine learning classification model can output a linear scale rating (e.g., a likely doctor rating between 0 and 10).

A "patient," as used herein, may be any subject (e.g., human, non-human, adult, child, etc.) and may be alternatively and equivalently referred to herein as a "patient" or a "subject." A "patient," as used herein, may but need not be a medical patient. A "patient," as used herein, may include a person who receives orthodontic treatment, including orthodontic treatment with a series of orthodontic aligners.

Any of the apparatuses and/or methods described herein may be part of a distal tooth scanning apparatus or method, or may be configured to work with a digital scanning apparatus or method.

As will be described in greater detail herein, automatically scoring the post-treatment tooth position (e.g., for each of a patient's teeth) may include collecting a 3D scan of the patient's teeth. Collecting the 3D scan may include taking the 3D scan, including scanning the patient's dental arch directly (e.g., using an intraoral scanner) or indirectly (e.g., scanning an impression of the patient's teeth), acquiring the 3D scan information from a separate device and/or third party, acquiring the 3D scan from a memory, or the like.

Additional information may be collected with the 3D scan, including patient information (e.g., age, gender, etc.).

The 3D scan information may be standardized and/or normalized. Standardizing the scan may include converting the 3D scan into a standard format (e.g., a tooth surface mesh), and/or expressing the 3D scan as a number of angles (e.g., vector angles) from a center point of each tooth, etc. In some variations, standardizing may include normalizing the 3D scan using another tooth, including stored tooth values.

The standardized 3D scan information may then be processed to extract one or more features that may be used to automatically score the post-treatment position of the teeth. This information may be used to automatically and accurately label the teeth of the 3D model, e.g., by numbering the teeth in a standard tooth numbering.

Note that although there are examples provided herein using PCA, other eigenvector-based multivariate analyses may be used. PCA is proposed because it may be automatically performed using know techniques including computing PCA using a correlation technique and/or a covariance technique, iterative methods including but not limited to non-linear iterative partial least squares techniques.

Standardizing may include identifying a predetermined number of angles relative to a center point of the target tooth. Any appropriate method may be used to determine the center of the tooth. For example, the center of the tooth may be determined from a mesh point representation of each tooth (e.g., from a segmented version of the 3D scan representing a digital model of the patient's teeth) by determining the geometric center of the mesh points for each tooth, by determining the center of gravity of the segmented tooth, etc. The same method for determining the center of each tooth may be consistently applied between the teeth and any teeth used to form (e.g., train) the systems described herein.

Standardizing may be distinct from normalizing. As used herein, standardizing may involve regularizing numerical and/or other description(s) of a tooth. For example, standardizing may involve regularizing the order and/or number of angles (from the center of the tooth) used to describe the teeth. The sizes of the teeth from the original 3D scan may be maintained.

Any appropriate features may be extracted from the prepared (e.g., standardized and/or normalized) teeth. For example, in some variations, features may include a principal component analysis (PCA) for each of the teeth in the dental arch being examined. Additional features (e.g., geometric descriptions of the patient's teeth) may not be necessary (e.g., PCA alone may be used) or it may be used to supplement the PCA of each tooth. PCA may be performed on the standardized teeth automatically using any appropriate technique, as discussed above, including using modules from existing software environments such C++ and C # (e.g., ALGLIB library that implements PCA and truncated PCA, MLPACK), Java (e.g., KNIME, Weka, etc.), Mathematica, MATLAB (e.g., MATLAB Statistics Toolbox, etc.), python (e.g., numpy, Scikit-learn, etc.), GNU Octave, etc.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1A:
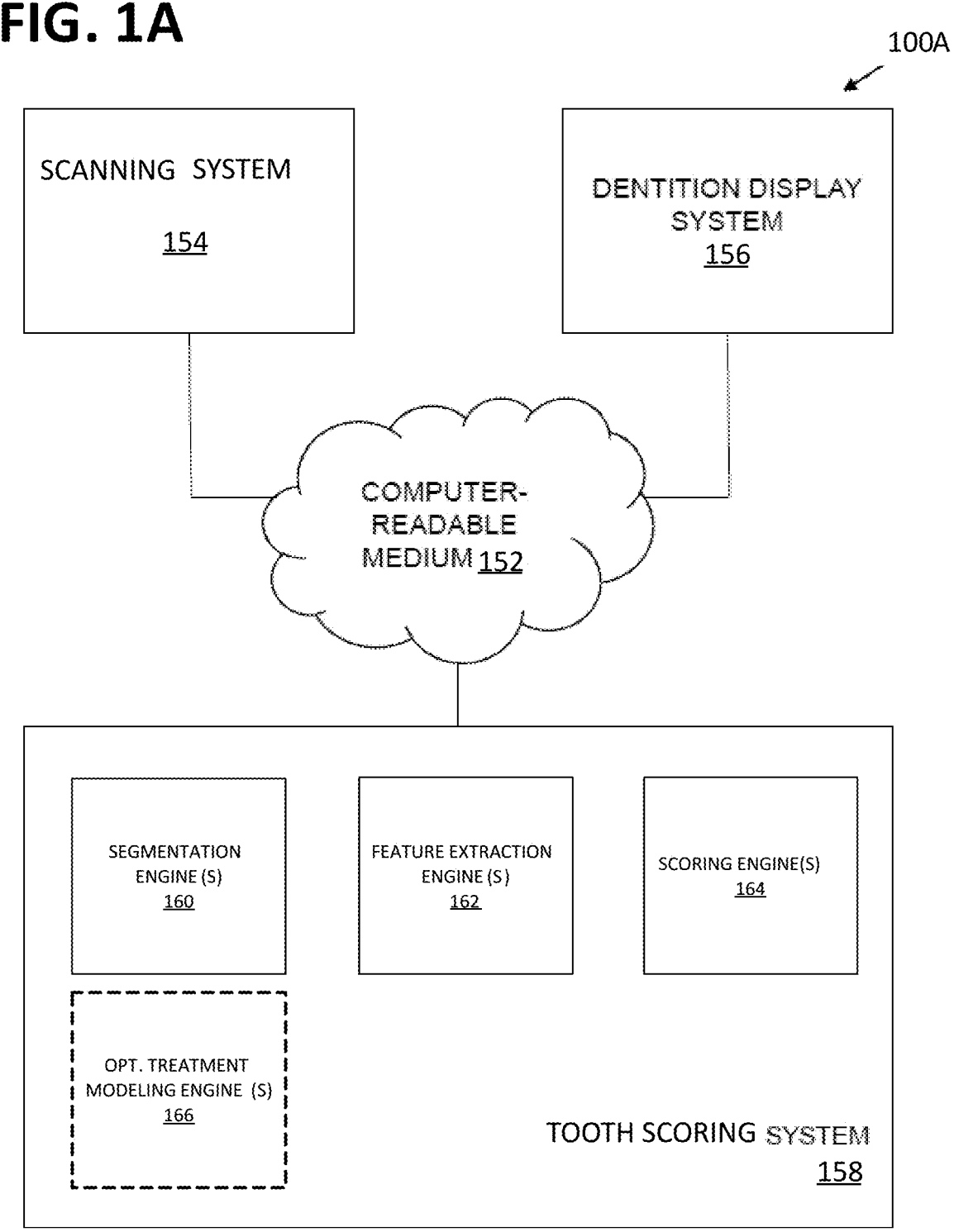
FIG. 1A is a diagram showing an example of a computing environment configured to digitally scan a dental arch and determine a post-treatment tooth position score.

Described herein are apparatuses (e.g., systems, computing device readable media, devices, etc.) and methods for scoring post-treatment tooth positions for a patient during treatment planning. One object of the present disclosure is to use machine learning technology to provide an automatic classifier that can assess tooth positions predicted by treatment planning software and assess the likelihood of whether the post-treatment tooth positions will be accepted or rejected by the doctor. The classifier can make this determination based upon data including patient demographics, tooth measurements, tooth surface mesh, processed tooth features, and historical patient data. These methods and apparatus can use this information to provide a tooth position scoring output to a patient, physician, dental technician, or the like.

For example, described herein are apparatuses and/or methods, e.g., systems, including systems to automatically implement processes that incorporate a tooth position scoring system. When the system is triggered by a request for a post-treatment tooth position score, the system can retrieve relevant tooth/patient information from a local or remote database, process the information, and convert the information into representative features. In some examples, the features can be formatted into a customized data structure that allows for guided exploration of neighboring teeth dependency and local/regional arch shape with a machine learning algorithm. The features or customized data structure can then be passed into tooth scoring classification model, which may use machine learning technology (e.g., Convolutional Neural Network (CNN), Decision Tree, Random Forest, Logistic Regression, Support Vector Machine, AdaBOOST, K-Nearest Neighbor (KNN), Quadratic Discriminant Analysis, Neural Network, etc.) to return a score on the post-treatment tooth position. The parameters inputted into the tooth scoring classification model can be optimized with historic data. The tooth scoring classification model may be used to provide an output indicating the likelihood that a post-treatment tooth position would be accepted or rejected by a doctor. The results may be provided on demand and/or may be stored in a memory (e.g., database) for later use.

The apparatuses and/or methods described herein may be useful in planning and fabrication of dental appliances, including elastic polymeric positioning appliances, is described in detail in U.S. Pat. No. 5,975,893, and in published PCT application WO 98/58596, which is herein incorporated by reference for all purposes. Systems of dental appliances employing technology described in U.S. Pat. No. 5,975,893 are commercially available from Align Technology, Inc., Santa Clara, Calif., under the tradename, INVISALIGN® System.

Throughout the body of the Description of Embodiments, the use of the terms "orthodontic aligner", "aligner", or "dental aligner" is synonymous with the use of the terms "appliance" and "dental appliance" in terms of dental applications. For purposes of clarity, embodiments are hereinafter described within the context of the use and application of appliances, and more specifically "dental appliances."

The apparatuses and/or methods (e.g., systems, devices, etc.) described below can be used with and/or integrated into an orthodontic treatment plan. The apparatuses and/or methods described herein may be used to segment a patient's teeth from a two-dimensional image and this segmentation information may be used to simulate, modify and/or choose between various orthodontic treatment plans. Segmenting the patient's teeth can be done automatically (e.g., using a computing device). For example, segmentation can be performed by a computing system automatically by evaluating data (such as three-dimensional scan, or a dental impression) of the patient's teeth or arch.

As described herein, an intraoral scanner may image a patient's dental arch and generate a virtual three-dimensional model of that dental arch. During an intraoral scan procedure (also referred to as a scan session), a user (e.g., a dental practitioner) of an intraoral scanner may generate multiple different images (also referred to as scans or medical images) of a dental site, model of a dental site, or other object. The images may be discrete images (e.g., point-and-shoot images) or frames from a video (e.g., a continuous scan). The three-dimensional scan can generate a 3D mesh of points representing the patient's arch, including the patient's teeth and gums. Further computer processing can segment or separate the 3D mesh of points into individual teeth and gums.

An automated tooth position scoring system, as used herein, may include a system that uses automated agents to identify and/or number individual teeth and/or dental features of virtual representations of teeth, such as teeth represented in a three-dimensional dental mesh model resulting from a digital scan. The present disclosure presents one or more novel processes for identifying and segmenting a patient's teeth during an identification process. Some implementations herein may solve technical problems related to optimizing and/or increasing the accuracy of digital dental scanning technologies.

FIG. 1A is a diagram showing an example of a computing environment 100A configured to facilitate gathering digital scans of a dental arch with teeth therein. The environment 100A includes a computer-readable medium 152, a scanning system 154, a dentition display system 156, and a 3D mesh processing system 158. One or more of the modules in the computing environment 100A may be coupled to one another or to modules not explicitly shown.

The computer-readable medium 152 and other computer readable media discussed herein are intended to represent a variety of potentially applicable technologies. For example, the computer-readable medium 152 can be used to form a network or part of a network. Where two components are co-located on a device, the computer-readable medium 152 can include a bus or other data conduit or plane. Where a first component is co-located on one device and a second component is located on a different device, the computer-readable medium 152 can include a wireless or wired back-end network or LAN. The computer-readable medium 152 can also encompass a relevant portion of a WAN or other network, if applicable.

The scanning system 154 may include a computer system configured to scan a patient's dental arch. A "dental arch," as used herein, may include at least a portion of a patient's dentition formed by the patient's maxillary and/or mandibular teeth, when viewed from an occlusal perspective. A dental arch may include one or more maxillary or mandibular teeth of a patient, such as all teeth on the maxilla or mandible or a patient. The scanning system 154 may include memory, one or more processors, and/or sensors to detect contours on a patient's dental arch. The scanning system 154 may be implemented as a camera, an intraoral scanner, an x-ray device, an infrared device, etc. The scanning system 154 may include a system configured to provide a virtual representation of a physical mold of patient's dental arch. The scanning system 154 may be used as part of an orthodontic treatment plan. In some implementations, the scanning system 154 is configured to capture a patient's dental arch at a beginning stage, an intermediate stage, etc. of an orthodontic treatment plan.

The dentition display system 156 may include a computer system configured to display at least a portion of a dentition of a patient. The dentition display system 154 may include memory, one or more processors, and a display device to display the patient's dentition. The dentition display system 156 may be implemented as part of a computer system, a display of a dedicated intraoral scanner, etc. In some implementations, the dentition display system 156 facilitates display of a patient's dentition using scans that are taken at an earlier date and/or at a remote location. It is noted the dentition display system 156 may facilitate display of scans taken contemporaneously and/or locally to it as well. As noted herein, the dentition display system 156 may be configured to display the intended or actual results of an orthodontic treatment plan applied to a dental arch scanned by the scanning system 154. The results may include 3D virtual representations of the dental arch, 2D images or renditions of the dental arch, etc.

The tooth scoring system 158 may include a computer system configured to process 3D scans or meshes of a patient's dentition taken by the scanning system 154. The tooth scoring system 158 may further be configured to process 2D images of the patient's detention. Additionally, 3D scans or meshes can be rendered into 2D image(s) from one or more viewing angles and input into the tooth scoring system 158. As noted herein, the tooth scoring system 158 may be configured to process scans of teeth in a dental arch. The tooth scoring system 158 may include segmentation engine(s) 160, feature extraction engine(s) 162, and scoring engine(s) 164. One or more of the modules of the image processing system 158 may be coupled to each other or to modules not shown.

As used herein, any "engine" may include one or more processors or a portion thereof. A portion of one or more processors can include some portion of hardware less than all of the hardware comprising any given one or more processors, such as a subset of registers, the portion of the processor dedicated to one or more threads of a multi-threaded processor, a time slice during which the processor is wholly or partially dedicated to carrying out part of the engine's functionality, or the like. As such, a first engine and a second engine can have one or more dedicated processors or a first engine and a second engine can share one or more processors with one another or other engines. Depending upon implementation-specific or other considerations, an engine can be centralized or its functionality distributed. An engine can include hardware, firmware, or software embodied in a computer-readable medium for execution by the processor. The processor transforms data into new data using implemented data structures and methods, such as is described with reference to the figures herein.

The engines described herein, or the engines through which the systems and devices described herein can be implemented, can be cloud-based engines. As used herein, a cloud-based engine is an engine that can run applications and/or functionalities using a cloud-based computing system. All or portions of the applications and/or functionalities can be distributed across multiple computing devices, and need not be restricted to only one computing device. In some embodiments, the cloud-based engines can execute functionalities and/or modules that end users access through a web browser or container application without having the functionalities and/or modules installed locally on the end-users' computing devices.

As used herein, "datastores" may include repositories having any applicable organization of data, including tables, comma-separated values (CSV) files, traditional databases (e.g., SQL), or other applicable known or convenient organizational formats. Datastores can be implemented, for example, as software embodied in a physical computer-readable medium on a specific-purpose machine, in firmware, in hardware, in a combination thereof, or in an applicable known or convenient device or system. Datastore-associated components, such as database interfaces, can be considered "part of" a datastore, part of some other system component, or a combination thereof, though the physical location and other characteristics of datastore-associated components is not critical for an understanding of the techniques described herein.

Datastores can include data structures. As used herein, a data structure is associated with a particular way of storing and organizing data in a computer so that it can be used efficiently within a given context. Data structures are generally based on the ability of a computer to fetch and store data at any place in its memory, specified by an address, a bit string that can be itself stored in memory and manipulated by the program. Thus, some data structures are based on computing the addresses of data items with arithmetic operations; while other data structures are based on storing addresses of data items within the structure itself. Many data structures use both principles, sometimes combined in non-trivial ways. The implementation of a data structure usually entails writing a set of procedures that create and manipulate instances of that structure. The datastores, described herein, can be cloud-based datastores. A cloud-based datastore is a datastore that is compatible with cloud-based computing systems and engines.

The segmentation engine(s) 160 may be configured to implement one or more automated agents configured to process tooth scans from the scanning system 154. The segmentation engine(s) 160 may include graphics engines to process images or scans of a dental arch. In some implementations, the segmentation engine(s) 160 format scan data from an scan of a dental arch into a dental mesh model (e.g., a 3D dental mesh model) of the dental arch. The segmentation engine(s) 160 may also be configured to segment the 3D dental mesh model of the dental arch into individual dental components, including segmenting the 3D dental mesh model into 3D mesh models of individual teeth. The 3D dental mesh models of the dental arch and/or the individual teeth may comprise geometric point clouds or polyhedral objects that depict teeth and/or other elements of the dental arch in a format that can be rendered on the dentition display system 156. In some embodiments, the 3D dental mesh models of the dental arch and/or the individual teeth can be rendered into a 2D image. The segmentation engine(s) 160 may provide 3D dental mesh models, the rendered 2D images, and/or other data to other modules of the 3D mesh processing system 158.

The feature extraction engine(s) 162 may implement one or more automated agents configured to extract dental features. A "dental feature," as used herein, may include data points from the 3D dental mesh model or the rendered 2D image(s) that correlate to edges, contours, vertices, vectors, or surfaces of the patient's teeth. A "dental feature" may be based on patient demographics and/or tooth measurements. A dental feature may be related to "PCA features," e.g., those dental features derived from a principal component analysis of a tooth. In some implementations, the feature extraction engine(s) 162 is configured to analyze 3D dental mesh models or the rendered 2D images from the segmentation engine(s) 160 to extract the dental features. In one implementation, the feature extraction engine(s) 162 may, for each tooth under consideration, extract a subset of dental features from the 3D dental mesh model or the rendered 2D image(s). For example, a specified number of tooth measurement points (e.g., nine tooth measurement points) can be extracted. This subset of measurement points can be selected to define the position and orientation of each tooth, as well as partial information on the tooth shape. By examining this subset of tooth measurement points across the whole tooth set of a patient, the system can identify underlying patterns in doctor-accepted tooth setups.

The feature extraction engine(s) 162 may further implement one or more automated agents configured to preprocess the extracted dental features. For example, processing of the extracted dental features may be required when a tooth is missing (data imputation needed, e.g., data interpolation, single point representation for the point cloud of the missing tooth, etc.), when a tooth needs to be extracted (data imputation needed, e.g., treated as missing tooth), when a tooth is flagged as "DO-NOT-MOVE" (Binary feature encoding), or when other requirements in treatment prescriptions exist (Direct feature encoding or additional preprocess steps, depending on the specific requirements). For example, missing teeth or teeth to be extracted can be represented by single points interpolated from neighboring teeth.

In some examples, the feature extraction engine(s) 162 may implement one or more automated agents configured to implement feature engineering to produce features for the scoring model. In one example, principal component analysis (PCA) can be implemented to obtain the dental features that will be used by the scoring model. In one implementation, the 3D dental mesh model or the rendered 2D image(s) of individual teeth comprises a scatter plot of points representing a patient's tooth, and PCA can be applied to the scatter plot to obtain vectors along the biggest distribution of scatter plots. In another example, the feature extraction engine(s) 162 may implement automated feature exploration (e.g., using deep neural networks or other feature selection methods) to produce the features for the scoring model. Alternatively or in combination, a third approach may include using both PCA and automated feature exploration (e.g., a hybrid approach) to produce the features that will be ultimately passed on to the scoring model.

The scoring engine(s) 164 may implement one or more automated agents configured to predict a post-treatment tooth position score using extracted and processed dental features. In some implementations, the scoring engine(s) 164 assign physical and/or geometrical properties to a 3D dental mesh model that are related to physical/geometrical properties of dental arches or teeth. The scoring engine(s) 164 may acquire dental features from the feature extraction engine(s) 162 and apply machine learning algorithms to predict a post-treatment tooth position score. In some implementations, the scoring engine(s) 164 use a trained convolutional neural network and/or trained classifiers to classify a target tooth into one or more identified categories of likely to be accepted by doctor, likely to be rejected by doctor, etc. Examples of machine learning systems implemented by the scoring engine(s) 164 may include Decision Tree, Random Forest, Logistic Regression, Support Vector Machine, Ada-BOOST, K-Nearest Neighbor (KNN), Quadratic Discriminant Analysis, Neural Network, etc., to determine a post-treatment tooth position score. The predicted score can be incorporated into a final segmentation result.

The optional treatment modeling engine(s) 166 may be configured to store and/or provide instructions to implement orthodontic treatment plans and/or the results of orthodontic treatment plans. The optional treatment modeling engine(s) 166 may provide the results of orthodontic treatment plans on a 3D dental mesh model. In some embodiments, the 3D dental mesh model can be rendered into one or more 2D image(s) from a plurality of viewing angles. The optional treatment modeling engine(s) 166 may model the results of application of orthodontic aligners to the patient's dental arch over the course of an orthodontic treatment plan.

Figure 1B:
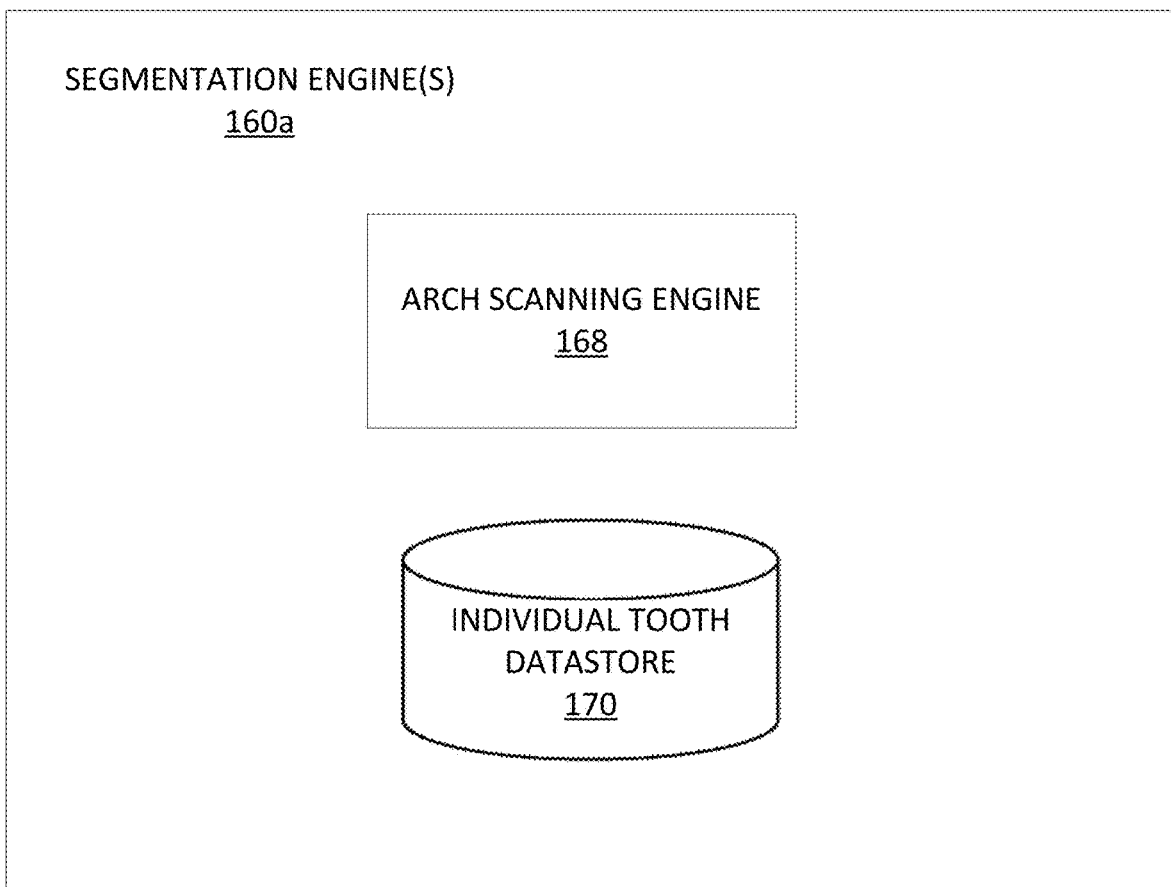
FIG. 1B is a diagram showing an example of segmentation engine(s).

FIG. 1B is a diagram showing an example of the segmentation engine(s) 160a. The segmentation engine(s) 160a may include an arch scanning engine 168 and an individual tooth segmentation datastore 170. One or more of the modules of the segmentation engine(s) 160a may be coupled to each other or to modules not shown.

The arch scanning engine 168 may implement one or more automated agents configured to scan a 3D dental mesh model or rendered 2D image(s) for individual tooth segmentation data. "Individual tooth segmentation data," as used herein, may include positions, geometrical properties (contours, etc.), and/or other data that can form the basis of segmenting individual teeth from 3D or 2D dental mesh models of a patient's dental arch. The arch scanning engine 168 may implement automated agents to separate dental mesh data for individual teeth from a 3D or 2D dental mesh model of the dental arch. The arch scanning engine 168 may further implement automated agents to number the individual teeth.

The individual tooth segmentation datastore 170 may be configured to store data related to model dental arches, including model dental arches that have been segmented into individual teeth. The model dental arch data may comprise data related to segmented individual teeth, including tooth identifiers of the individual teeth such as tooth types and tooth numbers.

Figure 1C:
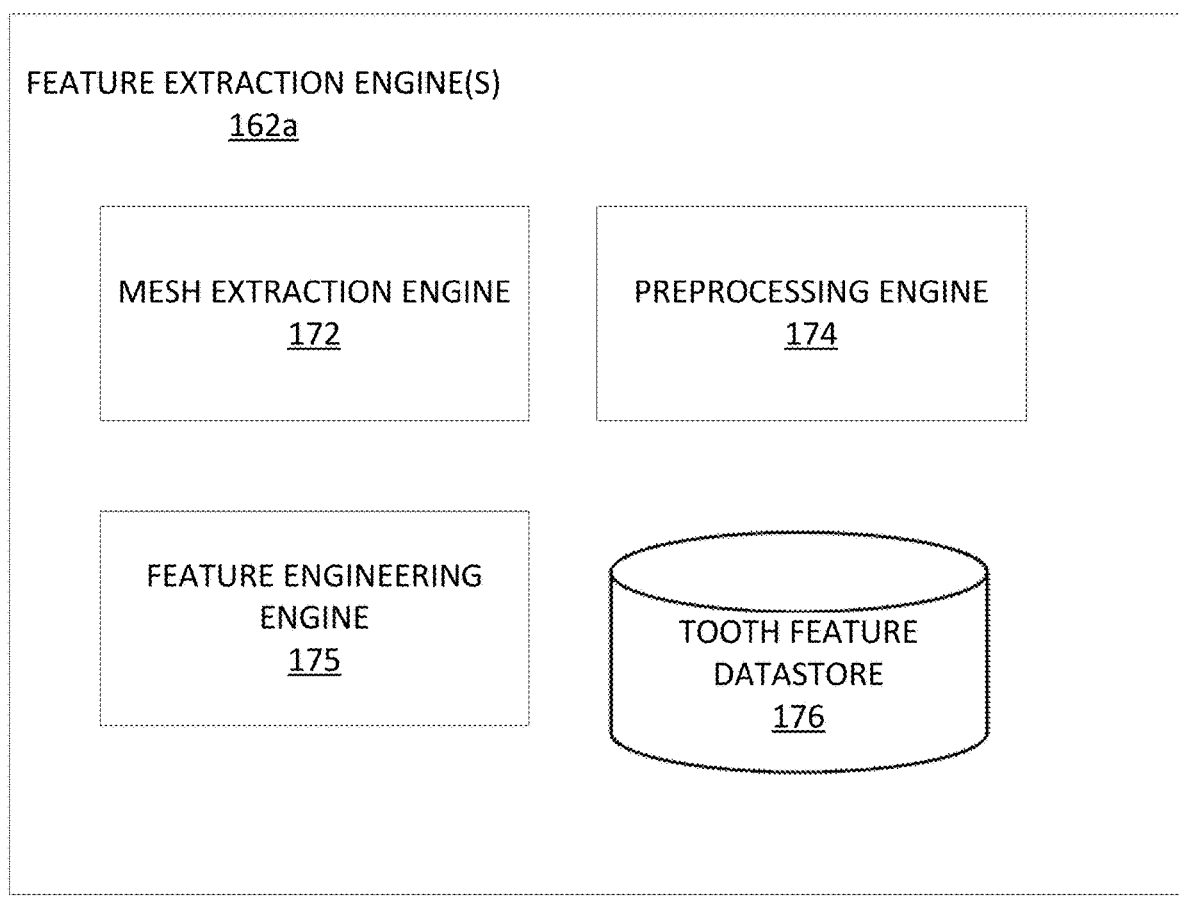
FIG. 1C is a diagram showing an example of a feature extraction engine(s).

FIG. 1C is a diagram showing an example of a feature extraction engine(s) 162a. The feature extraction engine(s) 162b may include mesh extraction engine 172, preprocessing engine 174, feature engineering engine 175, and a tooth feature datastore 176. One or more of the modules of the feature extraction engine(s) 162a may be coupled to each other or to modules not shown.

The mesh extraction engine 172 may implement one or more automated agents configured to determine or extract features from the individual tooth segmentation data. The tooth shape features may comprise, for example, the 3D point cloud, a subset of data points from the 3D point cloud specifically chosen to represent the shape, position, and orientation of the tooth, or datapoints from a 2D image rendered from the 3D point cloud. Table 1 below describes a subset of the 3D point cloud comprising nine tooth measurement points which can be extracted by the mesh extraction engine. These measurement points have been chosen to define the position and orientation of each tooth, as well as partial information on the tooth shape. By examining these tooth measurement points across the whole tooth set of a patient, the system can identify underlying patterns in doctor-accepted tooth setups. It should be understood that the entire 3D point cloud can be used, or alternatively another subset of points can be used that achieves the same goal of describing position, orientation, and shape of each tooth. The mesh extraction engine 172 can communicate the features to the tooth feature datastore 176.

TABLE 1

Definitions of selected tooth measurement points

| Point Name | Clinical Definition |
|---|---|
| FAPoint | Mid-point of FACC curve. For anterior teeth FA point is a natural center of the facial part of the clinical crown of |

TABLE 1-continued

Definitions of selected tooth measurement points

| Point Name | Clinical Definition |
| --- | --- |
| | the tooth. |
| RootCenter | The root center of the tooth. |
| CrownCenter | The crown center of the tooth. |
| TipPoint | Top most point of the FACC line. Tip of a tooth is a top most point of the tooth in direction of Occlusal Plane Normal. |
| ATipPoint | From tip point, the next local maxima point to the right. |
| BTipPoint | From tip point, the next local maxima point to the left. |
| ARidgePoint | Tooth A side of the ridge point. |
| BRidgePoint | Tooth B side of the ridge point. |
| GumPoint | Gingival, bottom most, point of the tooth in direction, normal to "Parameter_OcclusalPlane". |

Figure 2:
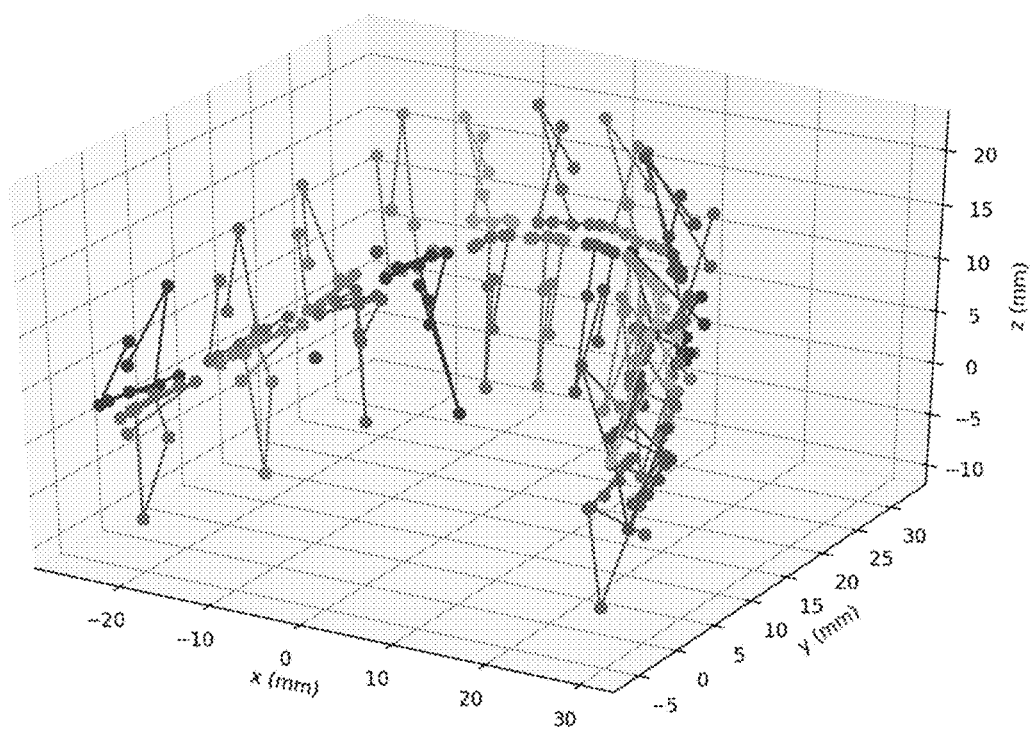
FIG. 2 shows one example of raw features extracted from a 3D point cloud of a patient's teeth.

FIG. 2 shows one example of raw features extracted from a 3D point cloud of a patient's teeth by the mesh extraction engine 172, specifically the nine points for each tooth as described in Table 1 above.

Figure 3A:
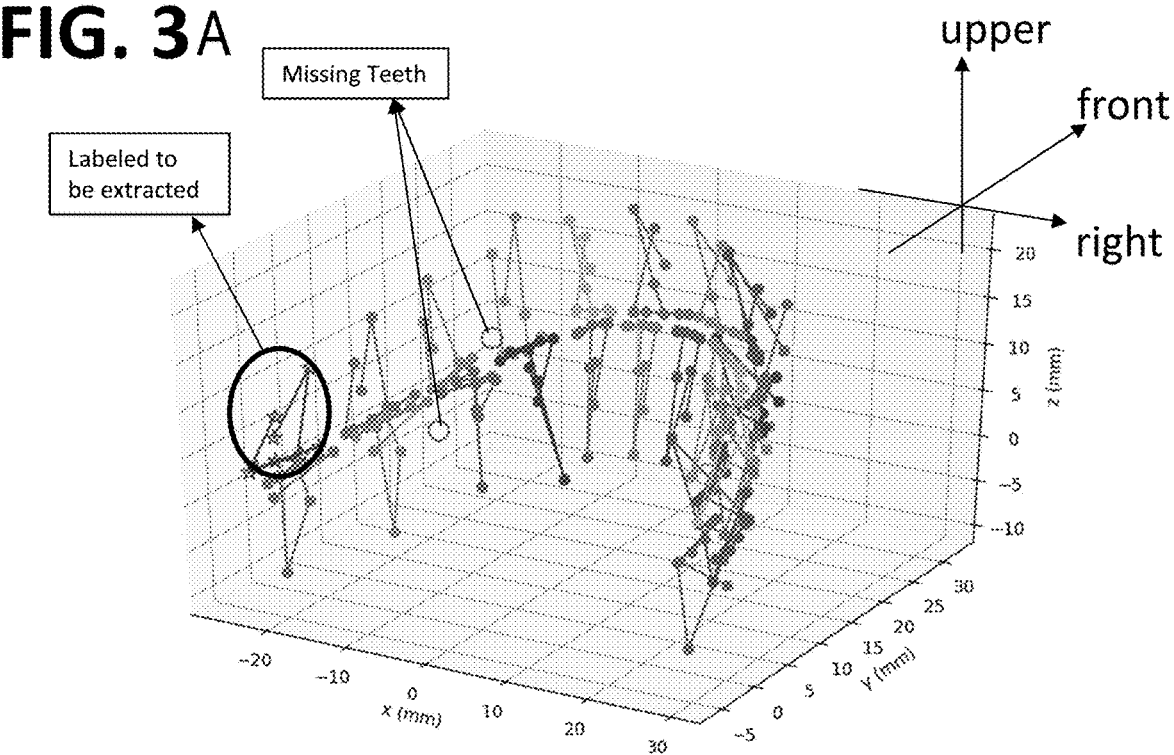
FIGS. 3A and 3B show one example of preprocessing the raw features extracted from the 3D point cloud of the patient's teeth.
Figure 3B:
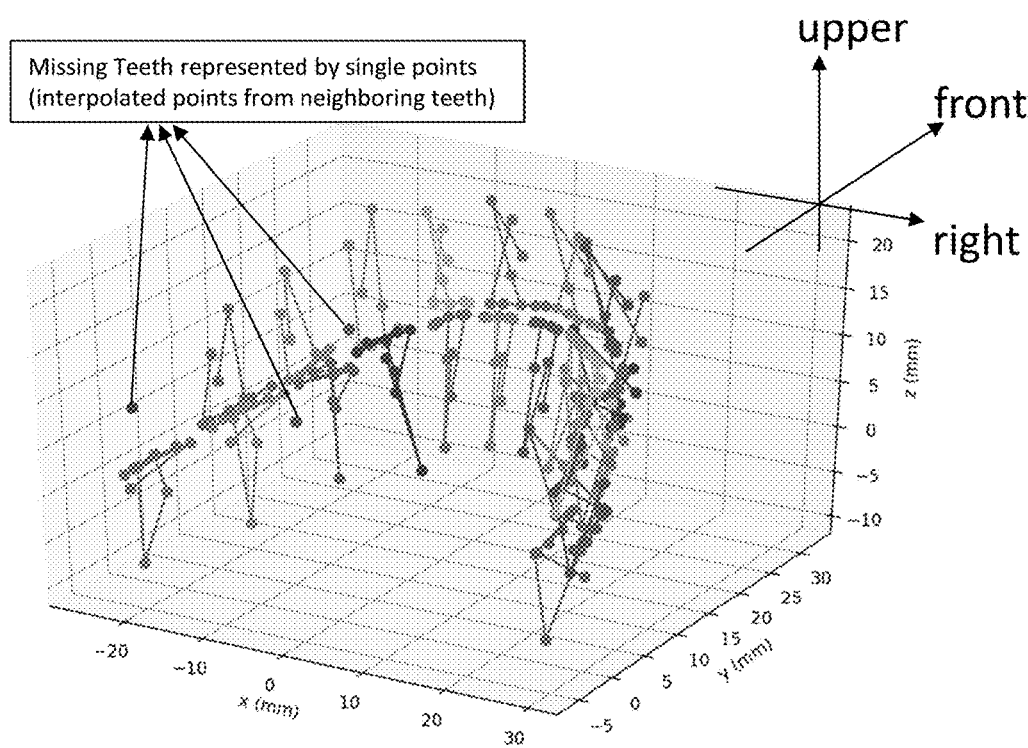

The preprocessing engine 174 may implement one or more automated agents configured to preprocess the extracted dental features. For example, preprocessing of the extracted dental features may be required when a tooth is missing (data imputation needed, e.g., data interpolation, single point representation for the point cloud of the missing tooth, etc.), when a tooth needs to be extracted (data imputation needed, e.g., treated as missing tooth), when a tooth is flagged as "DO-NOT-MOVE" (Binary feature encoding), or when other requirements in treatment prescriptions exist (Direct feature encoding or additional pre-process steps, depending on the specific requirements). For example, referring to FIGS. 3A and 3B, missing teeth or teeth to be extracted can be represented by single points interpolated from neighboring teeth. For each missing/to be extracted tooth i, (i∈T), the preprocessing engine can linearly extrapolate/interpolate from the tooth index set T, where T={2, 3, . . . , 15, 18, 19, . . . , 31} using universal tooth numbering, (depending on whether or not the tooth i is one of the end teeth {2, 15, 18, 31}, respectively) the crown center coordinates from crown centers of tooth i's immediate neighboring teeth, and assign all other tooth measurement points of the missing tooth i at the same location as the extrapolated/interpolated crown center position. In some implementations, the scoring model does not use wisdom teeth (indexed by {1, 16, 17, 31}). Essentially, the selected tooth measurement points (e.g., the nine chosen points from the 3D point cloud) of the missing tooth i collapse into a single point (which is the extrapolated/interpolated crown center), leading to a virtual tooth with zero geometric volume, i.e., a "singular" tooth. Preprocessing the extracted features allows for the input data into the scoring model to be consistent from case to case. For example, if the scoring model requires an input that includes the extracted features for 28 teeth, the preprocessing allows inputs into the scoring model for patients with missing or extracted teeth. The preprocessing engine 174 can communicate the normalization data to the tooth feature datastore 182.

The feature engineering engine 175 may implement one or more automated agents configured to implement feature engineering to produce features for the scoring model. In one example, principal component analysis (PCA) can be implemented to obtain the dental features that will be used by the scoring model. In one implementation, the 3D dental mesh model of individual teeth comprises a scatter plot of points representing a patient's tooth, and PCA can be applied to the scatter plot to obtain vectors along the biggest distribution of scatter plots. In another example, the feature engineering engine(s) 175 may implement automated feature exploration (e.g., using deep neural networks or other feature selection methods) to produce the features for the scoring model. Alternatively or in combination, a third approach may include using both PCA and automated feature exploration (e.g., a hybrid approach) to produce the features that will be ultimately passed on to the scoring model.

Figure 4:
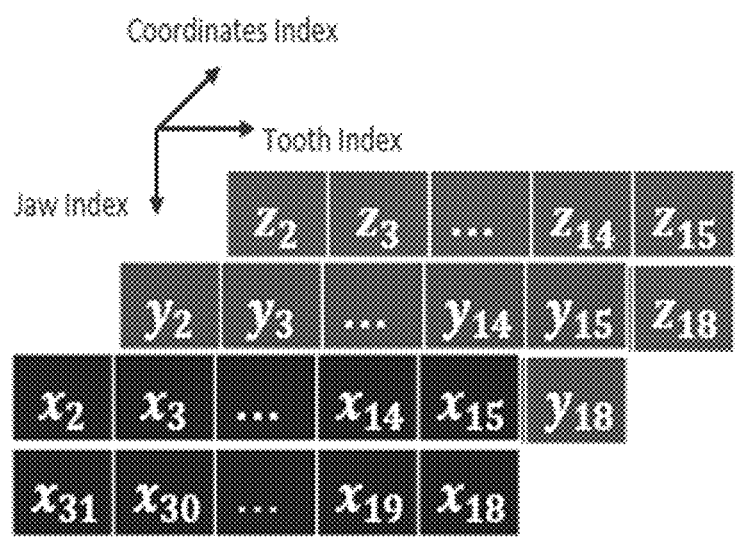
FIG. 4 shows an example of feature engineering used to format the extracted and preprocessed features into a special data format that is designed to store raw tooth point measurement data.

The feature engineering engine 175 can implement one or more automated agents configured to encode high level tooth position features, e.g., neighboring teeth dependency and local/regional arch shape, into the scoring system. In one implementation, the feature engineering engine 175 can format the extracted and preprocessed features into a special data format that is designed to store raw tooth point measurement data. Starting with the "FA-Point" data point from Table 1 above, let $X=\{x_t|t\in T\}$, $Y=\{y_t|t\in T\}$ and $Z=\{z_t|t\in T\}$ be the x,y,z-coordinates of FA-Points of the 28 teeth (denoted by T), respectively. By arranging x,y,z coordinates into three 2×14 matrices and stacking them along a third dimension, the feature engineering engine 175 can create a three-dimensional matrix that directly mimics the RGB image format, as shown in FIG. 4. The feature engineering engine can repeat the above data formatting process for all nine points of tooth measurements from Table 1 (or for each datapoint that is selected from the 3D point cloud) and stack the resulting matrices (each of size 2×14×3) along the "Jaw Index" dimension as indicated in FIG. 4, which leads to a 18×14×3 data matrix (or alternatively can be thought of as an 18×14 RGB image). The main advantage of this data formatting is that it allows guided exploration of neighboring teeth dependency and local/regional arch shape by machine learning algorithms.

The tooth feature datastore 176 may be configured to store data related to raw features, preprocessed raw features, and engineered features from the modules described above.

Figure 1D:
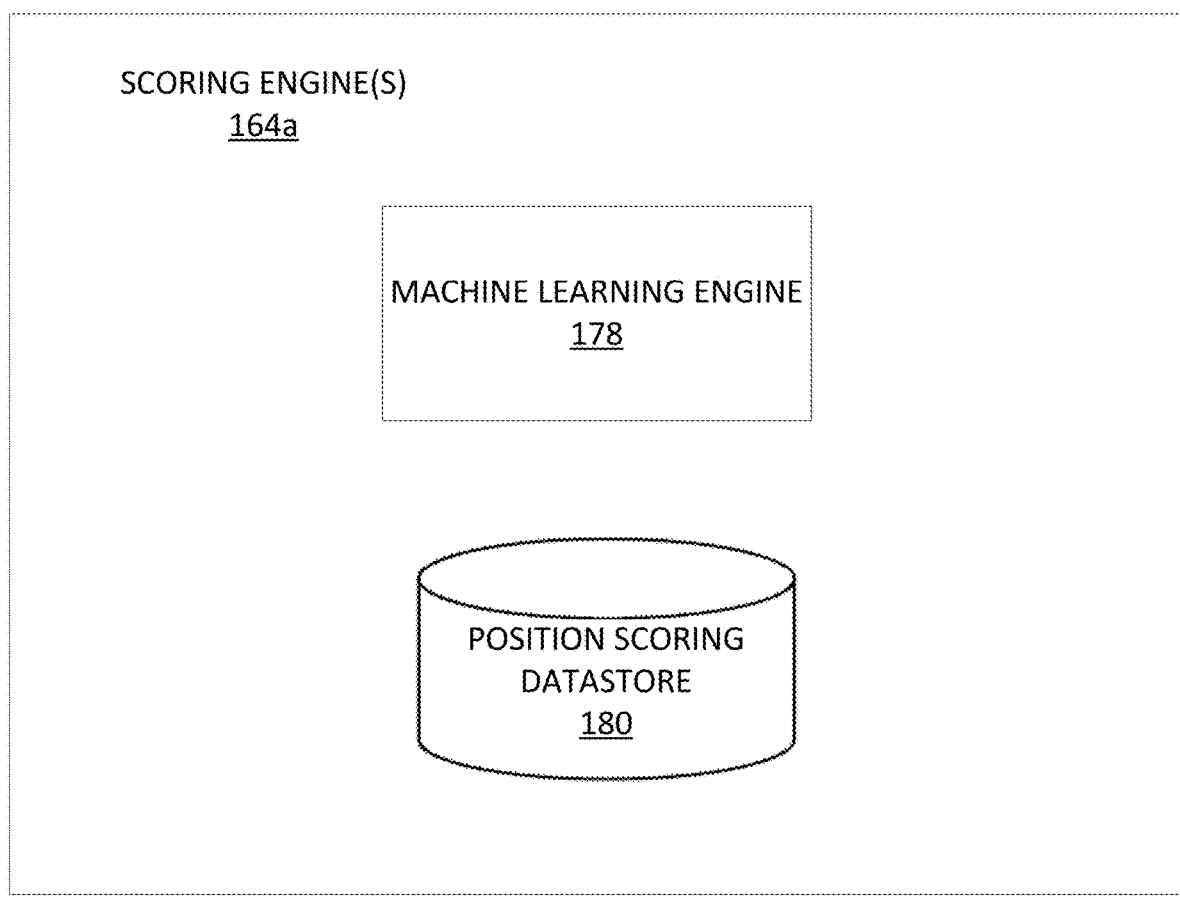
FIG. 1D is a diagram showing an example of a scoring engine(s).

FIG. 1D is a diagram showing an example of the scoring engine(s) 164a. The scoring engine(s) 164a may acquire raw features, preprocessed raw features, and engineered features data from the feature extraction engine(s) 162a described above. The scoring engine(s) 164a may include a machine learning engine 178 and a position scoring datastore 180.

The machine learning engine 178 may implement one or more automated agents configured to use machine learning techniques to classify a post-treatment position of a patient's teeth. In some implementations, the machine learning engine 178 may acquire raw features, preprocessed raw features, and engineered features data from the feature extraction engine(s) 162a. Using a trained classifier, the machine learning engine 178 may provide an identifier (e.g., a statistical or other score) that associates the post-treatment position of the patient's teeth with a specified category of tooth position scoring. As examples, the machine learning engine 178 may use a classifier trained to correlate various dental features with whether the post-treatment teeth position is likely to be accepted or rejected by the patient's doctor. The machine learning engine 178 may incorporate one or more machine learning techniques. Examples of such techniques include Convolutional Neural Networks (CNN), Decision Tree, Random Forest, Logistic Regression, Support Vector Machine, AdaBOOST, K-Nearest Neighbor (KNN), Quadratic Discriminant Analysis, Neural Network, etc. The machine learning engine 178 can provide an output with a post-treatment tooth position score. The output can be, for example, a binary score or a linear score.

The position scoring datastore 180 may be configured to store data relating to the post-treatment tooth position score from the machine learning engine 178 (e.g., the output from the machine learning engine). In some implementations, the post-treatment tooth position score is a binary labeling score (e.g., a score of 1 for a post-treatment tooth position that is likely to be accepted by a doctor and a score of 0 for a post-treatment tooth position that is likely to be rejected by a doctor). In other implementations, the post-treatment tooth position score is a linear labeling score (e.g., a score ranging from 0 to 10, where 0 indicates that a doctor is likely to reject the post-treatment tooth position and a score of 10 indicates that a doctor is likely to accept the post-treatment tooth position).

Figure 1E:
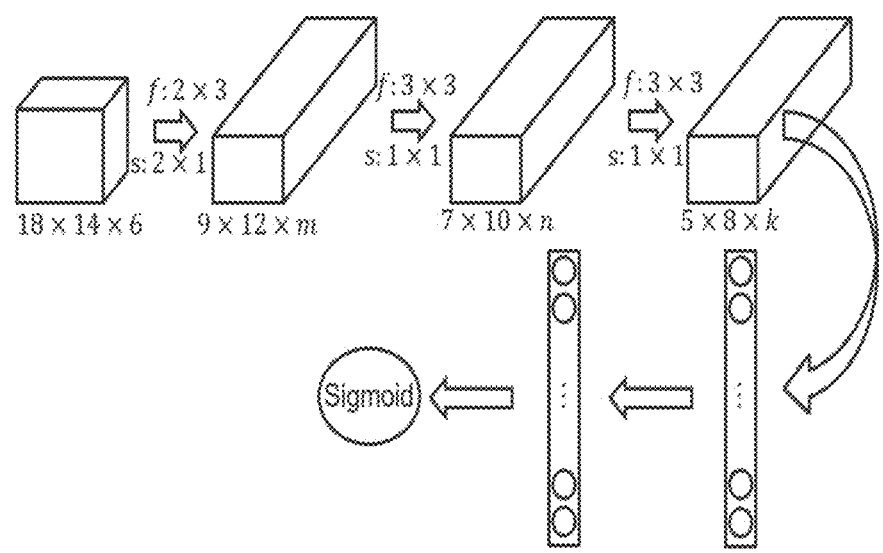
FIG. 1E is an example of one implementation of a scoring engine that comprises a Convolutional Neural Network (CNN).

FIG. 1E is a schematic diagram illustrating one example of determining a post-treatment tooth position score when the machine learning engine comprises a Convolutional Neural Network (CNN). Starting from the input matrix (e.g., the input matrix from the feature engineering engine as also illustrated in FIG. 4), the CNN model architecture may include three convolutional layers, followed by two fully connected layers before the final "sigmoid" node (which outputs a single value between [0, 1], indicating the probability of a given input being accepted by a doctor).

By design, the first convolutional layer examines each of the selected tooth measurement points across a specified number of neighboring teeth (e.g., three neighboring teeth from left to right in both upper and lower jaws). In addition, it also compares the initial tooth positions of a patient with positions to-be-scored (Note there are 6 channels along the $3^{rd}$ dimension of the input, the first 3 channels correspond to positions-to-be-scored, while the last 3 channels correspond to the patient's initial tooth positions). The second and third convolutional layers examine higher level features, including the relationship between different tooth measurement points, as well as local arch across neighboring teeth. The two fully connected layers can then aggregate all features from the convolutional layers and output a final probability estimate of a given input being accepted by a doctor.

Figure 5:
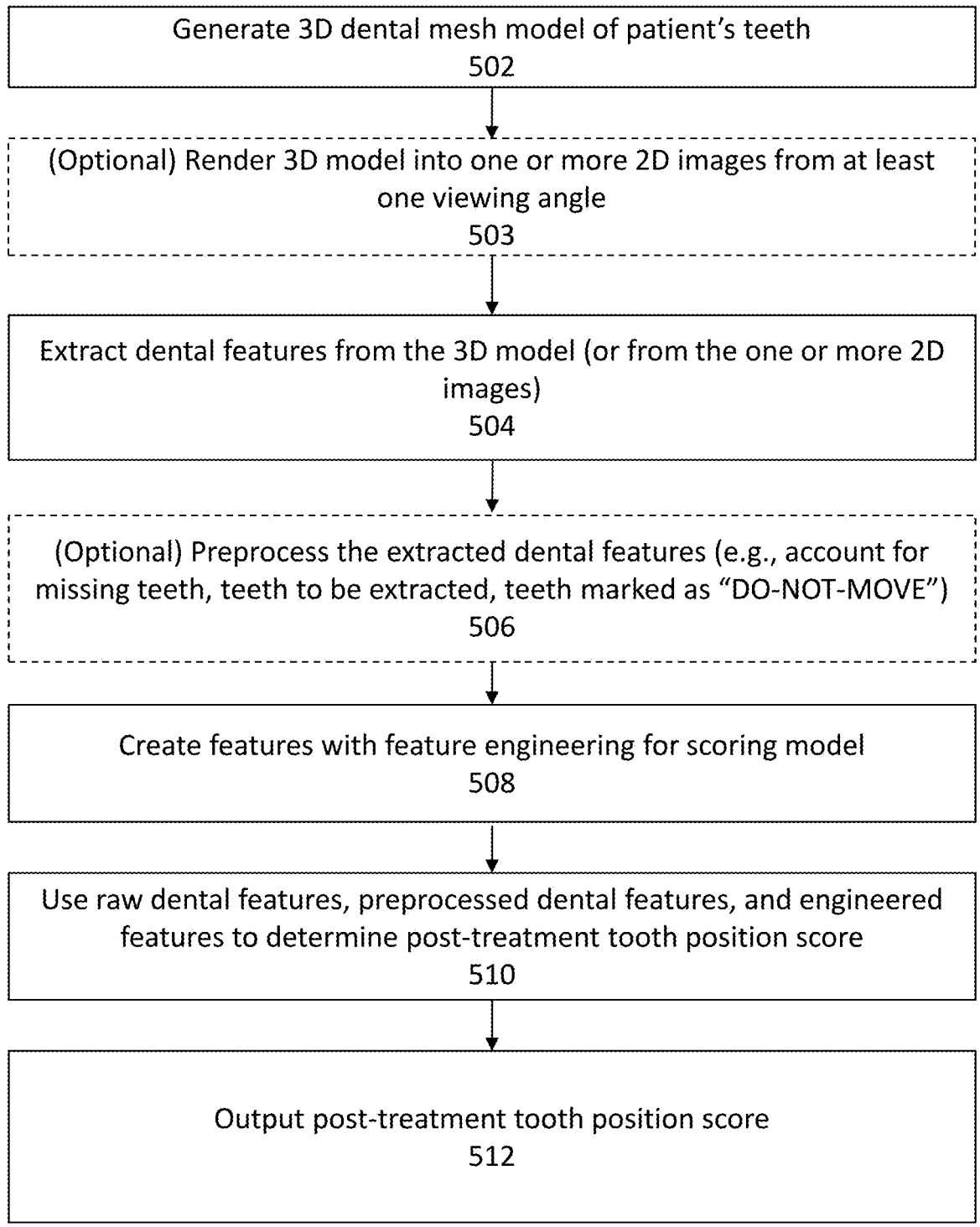
FIG. 5 is a flowchart describing one example of determining a post-treatment tooth position score.

FIG. 5 illustrates one example of a method for automatically providing a post-treatment tooth position score for a patient's dental arch. This method may be automatically implemented by a system, such as one or more of the systems in the computing environment 100A, shown in FIG. 1A. At an operation 502, the system may automatically collect a three-dimensional (3D) scan of the patient's dental arch. The 3D scan may be collected directly from the patient (e.g., using an intraoral scanner) or indirectly (e.g., by scanning a mold of the patient's dentition and/or be receiving a digital model of the patient taken by another, etc.). The 3D scan can be used to generate a 3D dental mesh model of the patient's teeth.

The 3D scan may be prepared for further processing. For example, the 3D scan may be expressed as a digital mesh and/or segmented into individual teeth (and non-teeth elements, such as gingiva, arch, etc.). Optionally, at step 503, the 3D dental mesh model of the patient's teeth may be rendered into one or more 2D images. The 2D images can be rendered from multiple viewing angles within the 3D dental mesh model.

At an operation 504, raw dental features may be extracted from the 3D model of the patient's teeth (and in some variations from additional data about the patient or the patient's teeth or from prescription guidelines), e.g., using a feature extraction engine. If the 3D dental mesh model is rendered into 2D images at optional operation 503, the feature extraction engine can extract raw dental features from the rendered 2D images. For example, features from the individual tooth segmentation data may be extracted with the feature extraction engine. The tooth shape features may comprise, for example, the 3D point cloud, a subset of data points from the 3D point cloud specifically chosen to represent the shape, position, and orientation of the tooth, or data points from the rendered 2D images.

At an operation 506, the raw dental features may optionally be preprocessed. Some preprocessing might be needed, depending on the patient's teeth and/or descriptions in treatment prescriptions. For example, preprocessing may be required when a patient has 1) a tooth that is missing (data imputation needed, e.g., data interpolation, single point representation for the point cloud of the missing tooth, etc.), 2) a tooth that needs to be extracted (data imputation needed, e.g., treated as missing tooth), 3) a tooth that is flagged as "DO-NOT-MOVE" (Binary feature encoding), or 4) other requirements in treatment prescriptions (Direct feature encoding or additional preprocess steps, depending on the specific requirements). For example, the preprocessing engine can collapse selected tooth measurement points for a missing/to be extracted/etc. tooth into a single point leading to a virtual tooth with zero geometric volume.

At an operation 508, additional features for the scoring model may be created with feature engineering. In one example, principal component analysis (PCA) can be implemented to obtain the dental features that will be used by the scoring model. In one implementation, the 3D dental mesh model of individual teeth comprises a scatter plot of points representing a patient's tooth, and PCA can be applied to the scatter plot to obtain vectors along the biggest distribution of scatter plots. In another example, the feature engineering engine may implement automated feature exploration (e.g., using deep neural networks or other feature selection methods) to produce the features for the scoring model. Alternatively or in combination, a third approach may include using both PCA and automated feature exploration (e.g., a hybrid approach) to produce the features that will be ultimately passed on to the scoring model.

Additionally, at the operation 508 the feature engineering engine can format the extracted and preprocessed features into a special data format that is designed to store raw tooth point measurement data configured to allow machine learning/deep learning models (e.g., the convolutional neural network) to encode high level tooth position features.

At an operation 510, extracted dental features, the preprocessed features, and the engineered features may be used exclusively or in combination with any other extracted feature described herein. The dental features may be provided to the scoring engine to determine the post-treatment tooth position score that indicates how likely a post-treatment tooth position is to be accepted or rejected by the doctor.

At an operation 512, the post-treatment tooth position score may then be output. In some variations this information is used to modify a model (e.g., a 3D digital model) of the patient's teeth (e.g., dental arch). For example, each tooth may be labeled and/or referenced by a name or number (or other alphanumeric) that corresponds to the post-treatment tooth position score. For example, the tooth may be automatically and accurately labeled using these methods and systems in a numbering standard (e.g., a universal number system or a modified universal numbering system) that further indicates the post-treatment tooth position score. For example, uppercase letters A through T may be used for primary teeth and the numbers 1-32 may be used for permanent teeth, as would be understood by those of skill in the dental/orthodontic art. Alternative standard dental numbering systems may be used (e.g., FDI World Dental Federation notation, Palmer notation, etc.).

Figure 6:
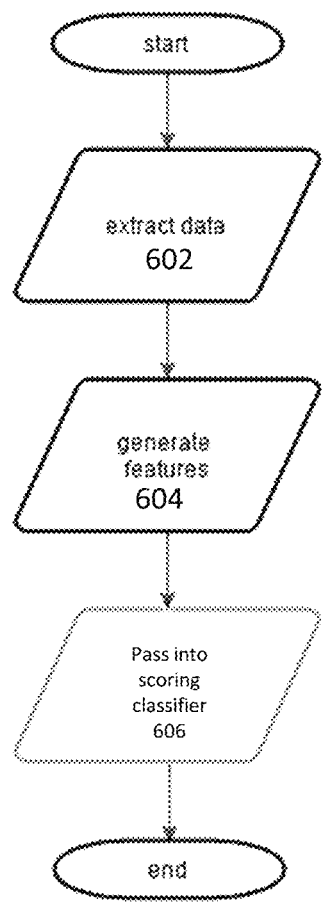
FIG. 6 is another flowchart describing one example of determining a post-treatment tooth position score.

FIG. 6 is another flowchart that shows the overall scoring system described above and describes a method of extracting and generating data to be passed into a post-treatment tooth position scoring system.

At an operation 602 of FIG. 6, data can be extracted for use by the scoring system. The data can include patient teeth data (e.g., 3D model/scanning of teeth/2D images rendered from the 3D dental mesh model) as well as clinical data about the patient (e.g., patient age, gender, prescription information, etc.). Next, at step 604 of FIG. 6, the detection system can generate features from the extracted data, including raw tooth features, preprocessed features, and engineered features, as described above. Finally, at step 606 of FIG. 6, the features can be passed into the scoring classifier to determine a post-treatment tooth position score.

Figure 7:
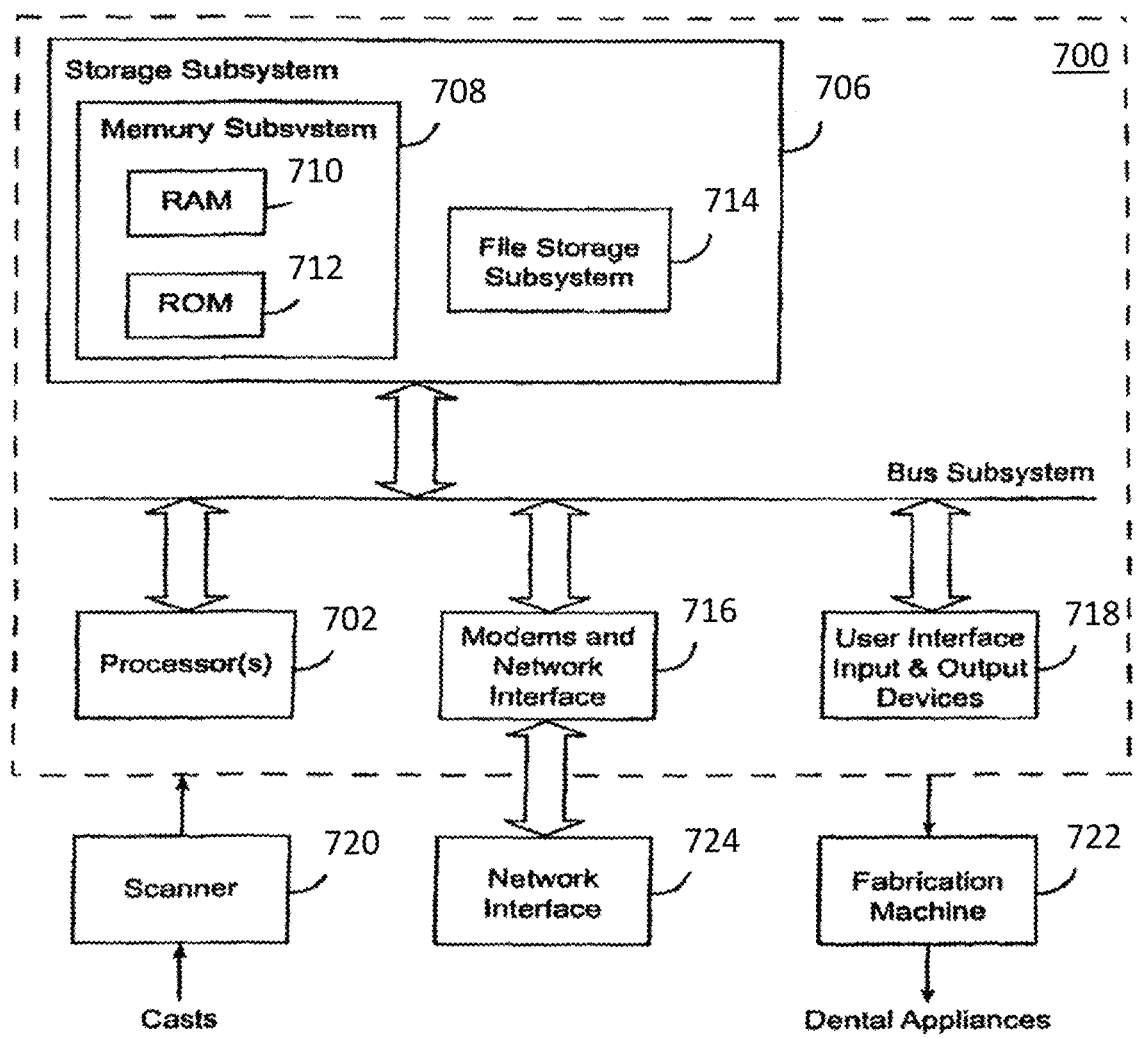
FIG. 7 is a simplified block diagram of a data processing system that may perform the methods described herein.

The methods described herein may be performed by an apparatus, such as a data processing system, which may include hardware, software, and/or firmware for performing many of these steps described above. For example, FIG. 7 is a simplified block diagram of a data processing system 700. Data processing system 700 typically includes at least one processor 702 which communicates with a number of peripheral devices over bus subsystem 704. These peripheral devices typically include a storage subsystem 706 (memory subsystem 708 and file storage subsystem 714), a set of user interface input and output devices 718, and an interface to outside networks 716, including the public switched telephone network. This interface is shown schematically as "Modems and Network Interface" block 716, and is coupled to corresponding interface devices in other data processing systems over communication network interface 724. Data processing system 700 may include a terminal or a low-end personal computer or a high-end personal computer, workstation or mainframe.

The user interface input devices typically include a keyboard and may further include a pointing device and a scanner. The pointing device may be an indirect pointing device such as a mouse, trackball, touchpad, or graphics tablet, or a direct pointing device such as a touchscreen incorporated into the display. Other types of user interface input devices, such as voice recognition systems, may be used.

User interface output devices may include a printer and a display subsystem, which includes a display controller and a display device coupled to the controller. The display device may be a cathode ray tube (CRT), a flat-panel device such as a liquid crystal display (LCD), or a projection device. The display subsystem may also provide nonvisual display such as audio output.

Storage subsystem 706 maintains the basic programming and data constructs that provide the functionality of the present invention. The software modules discussed above are typically stored in storage subsystem 706. Storage subsystem 706 typically comprises memory subsystem 708 and file storage subsystem 714.

Memory subsystem 708 typically includes a number of memories including a main random access memory (RAM) 710 for storage of instructions and data during program execution and a read only memory (ROM) 712 in which fixed instructions are stored. In the case of Macintosh-compatible personal computers the ROM would include portions of the operating system; in the case of IBM-compatible personal computers, this would include the BIOS (basic input/output system).

File storage subsystem 714 provides persistent (nonvolatile) storage for program and data files, and typically includes at least one hard disk drive and at least one floppy disk drive (with associated removable media). There may also be other devices such as a CD-ROM drive and optical drives (all with their associated removable media). Additionally, the system may include drives of the type with removable media cartridges. The removable media cartridges may, for example be hard disk cartridges, such as those marketed by Syquest and others, and flexible disk cartridges, such as those marketed by Iomega. One or more of the drives may be located at a remote location, such as in a server on a local area network or at a site on the Internet's World Wide Web.

In this context, the term "bus subsystem" is used generically so as to include any mechanism for letting the various components and subsystems communicate with each other as intended. With the exception of the input devices and the display, the other components need not be at the same physical location. Thus, for example, portions of the file storage system could be connected over various local-area or wide-area network media, including telephone lines. Similarly, the input devices and display need not be at the same location as the processor, although it is anticipated that the present invention will most often be implemented in the context of PCS and workstations.

Bus subsystem 704 is shown schematically as a single bus, but a typical system has a number of buses such as a local bus and one or more expansion buses (e.g., ADB, SCSI, ISA, EISA, MCA, NuBus, or PCI), as well as serial and parallel ports. Network connections are usually established through a device such as a network adapter on one of these expansion buses or a modem on a serial port. The client computer may be a desktop system or a portable system.

Scanner 720 is responsible for scanning casts of the patient's teeth obtained either from the patient or from an orthodontist and providing the scanned digital data set information to data processing system 700 for further processing. In a distributed environment, scanner 720 may be located at a remote location and communicate scanned digital data set information to data processing system 700 over network interface 724.

Fabrication machine 722 fabricates dental appliances based on intermediate and final data set information acquired from data processing system 700. In a distributed environment, fabrication machine 722 may be located at a remote location and acquire data set information from data processing system 700 over network interface 724.

Various alternatives, modifications, and equivalents may be used in lieu of the above components. Although the final position of the teeth may be determined using computer-aided techniques, a user may move the teeth into their final positions by independently manipulating one or more teeth while satisfying the constraints of the prescription.

Additionally, the techniques described here may be implemented in hardware or software, or a combination of the two. The techniques may be implemented in computer programs executing on programmable computers that each includes a processor, a storage medium readable by the processor (including volatile and nonvolatile memory and/or storage elements), and suitable input and output devices. Program code is applied to data entered using an input device to perform the functions described and to generate output information. The output information is applied to one or more output devices.

Each program can be implemented in a high level procedural or object-oriented programming language to operate in conjunction with a computer system. However, the programs can be implemented in assembly or machine language, if desired. In any case, the language may be a compiled or interpreted language.

Each such computer program can be stored on a storage medium or device (e.g., CD-ROM, hard disk or magnetic diskette) that is readable by a general or special purpose programmable computer for configuring and operating the computer when the storage medium or device is read by the computer to perform the procedures described. The system also may be implemented as a computer-readable storage medium, configured with a computer program, where the storage medium so configured causes a computer to operate in a specific and predefined manner.

Thus, any of the methods (including user interfaces) described herein may be implemented as software, hardware or firmware, and may be described as a non-transitory computer-readable storage medium storing a set of instructions capable of being executed by a processor (e.g., computer, tablet, smartphone, etc.), that when executed by the processor causes the processor to control perform any of the steps, including but not limited to: displaying, communicating with the user, analyzing, modifying parameters (including timing, frequency, intensity, etc.), determining, alerting, or the like.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. Numerous different combinations of embodiments described herein are possible, and such combinations are considered part of the present disclosure. In addition, all features discussed in connection with any one embodiment herein can be readily adapted for use in other embodiments herein. It is intended that the following claims define the scope of the invention and that methods and structures within the scope of these claims and their equivalents be covered thereby.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and/or methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the patient matter may be practiced. As mentioned, other embodiments may be utilized and derived there from, such that structural and logical substitutions and changes may be made without departing from the scope of this disclosure. Such embodiments of the inventive patient matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of automatically determining a post-treatment tooth position score of a patient's teeth, the method comprising the steps of:

acquiring, in a computing device, a three-dimensional (3D) model of the patient's teeth;
    determining, in the computing device, raw features of the patient's teeth from the 3D model of the patient's teeth;
    creating, in the computing device, engineered features from the raw features of the patient's teeth;
    applying the engineered features to a binary classifier, a linear classifier, or some combination thereof, of the computing device; and
    outputting from the computing device the post-treatment tooth position score of the patient's teeth.

2. The method of claim 1, further comprising processing, in the computing device, the raw features of the patient's teeth to account for missing teeth, teeth to be extracted, or teeth that are not to be moved during treatment.

3. The method of claim 1, wherein outputting comprises outputting a binary score indicating that a doctor is likely to reject the post-treatment tooth position or accept the post-treatment tooth position.

4. The method of claim 1, wherein outputting comprises outputting a linear score indicating along a scale how likely a doctor is to accept or reject the post-treatment tooth position.

5. The method of claim 1, wherein the creating engineered features step further comprises taking a principal component analysis (PCA) of the raw features of the patient's teeth.

6. The method of claim 1, wherein the creating engineered features step further comprises which performing automated feature exploration of neighboring teeth dependency and local/regional arch shape from the raw features of the patient's teeth.

7. The method of claim 6, wherein the automated feature exploration is performed with a neural network.

8. The method of claim 1, wherein the creating engineered features step further comprises taking a principal component analysis (PCA) of the raw features of the patient's teeth and performing automated feature exploration of neighboring teeth dependency and local/regional arch shape from the raw features of the patient's teeth.

9. The method of claim 1, further comprises taking the 3D model of the patient's teeth.

10. The method of claim 9, wherein the 3D model is acquired from a three-dimensional scanner.

11. The method of claim 9, wherein the 3D model is acquired from a mold of the patient's teeth.

12. A non-transitory computing device readable medium having instructions stored thereon for determining a post-treatment tooth position score of a patient's teeth, wherein the instructions are executable by a processor to cause a computing device to:

acquire a three-dimensional (3D) model of the patient's teeth;
    determine raw features of the patient's from the 3D model of the patient's teeth;
    create engineered features from the raw features of the patient's teeth;
    apply the engineered features to a binary classifier, a linear classifier, or some combination thereof, of the computing device; and
    output the post-treatment tooth position score of the patient's teeth.

13. The non-transitory computing device readable medium of claim 12, wherein the instructions are further configured to process the raw features of the patient's teeth to account for missing teeth, teeth to be extracted, or teeth that are not to be moved during treatment.

14. The non-transitory computing device readable medium of claim 12, wherein the instructions are further configured so that the output is a binary score indicating that a doctor is likely to reject the post-treatment tooth position or accept the post-treatment tooth position.

15. The non-transitory computing device readable medium of claim 12, wherein the instructions are further configured so that the output is a linear score indicating along a scale how likely a doctor is to accept or reject the post-treatment tooth position.

16. The non-transitory computing device readable medium of claim 12, wherein the instructions are further configured to create engineered features by taking a principal component analysis (PCA) of the raw features of the patient's teeth.

17. The non-transitory computing device readable medium of claim 12, wherein the instructions are further configured to create engineered features by performing automated feature exploration of neighboring teeth dependency and local/regional arch shape from the raw features of the patient's teeth.

18. The non-transitory computing device readable medium of claim 12, wherein the instructions are further configured to create engineered features by taking a principal component analysis (PCA) of the raw features of the patient's teeth and further configured to create engineered features by performing automated feature exploration of neighboring teeth dependency and local/regional arch shape from the raw features of the patient's teeth.

19. The non-transitory computing device readable medium of claim 17 wherein the automated feature exploration is performed with a neural network.

20. The non-transitory computing device readable medium of claim 12, wherein the instructions are further configured to acquire the 3D model from a three-dimensional scanner.

21. A method of automatically determining a post-treatment tooth position score of a patient's teeth, the method comprising the steps of:
   acquiring, in a computing device, a three-dimensional (3D) model of the patient's teeth;
   rendering the 3D model of the patient's teeth into one or more 2D images of the patient's teeth;
   determining, in the computing device, raw features of the patient's teeth from the one or more 2D images;
   creating, in the computing device, engineered features from the raw features of the patient's teeth;
   applying the engineered features to a binary classifier, a linear classifier, or some combination thereof, of the computing device; and
   outputting from the computing device the post-treatment tooth position score of the patient's teeth.

22. The method of claim 21, further comprising processing, in the computing device, the raw features of the patient's teeth to account for missing teeth, teeth to be extracted, or teeth that are not to be moved during treatment.

23. The method of claim 22, wherein outputting comprises outputting a binary score indicating that a doctor is likely to reject the post-treatment tooth position or accept the post-treatment tooth position.

24. The method of claim 22, wherein outputting comprises outputting a linear score indicating along a scale how likely a doctor is to accept or reject the post-treatment tooth position.

* * * * *